(12) United States Patent
Sung et al.

(10) Patent No.: US 11,278,630 B2
(45) Date of Patent: Mar. 22, 2022

(54) ORAL DRUG COMPOSITION AND USE THEREOF

(71) Applicant: National Tsing Hua University, Hsinchu (TW)

(72) Inventors: Hsing-Wen Sung, Hsinchu (TW); Yang-Bao Miao, Hsinchu (TW); Kuan-Hung Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 78 days.

(21) Appl. No.: 16/810,983

(22) Filed: Mar. 6, 2020

(65) Prior Publication Data

US 2021/0069344 A1    Mar. 11, 2021

(30) Foreign Application Priority Data

Sep. 10, 2019 (TW) ................................. 108132636

(51) Int. Cl.
*A61K 47/69* (2017.01)
*A61K 47/54* (2017.01)
*A61P 35/00* (2006.01)
*A61K 31/4188* (2006.01)

(52) U.S. Cl.
CPC ...... *A61K 47/6901* (2017.08); *A61K 31/4188* (2013.01); *A61K 47/54* (2017.08); *A61K 47/545* (2017.08); *A61P 35/00* (2018.01)

(58) Field of Classification Search
None
See application file for complete search history.

(56) References Cited

FOREIGN PATENT DOCUMENTS

JP    2005204612 A  *  8/2005

\* cited by examiner

*Primary Examiner* — Joseph R Kosack
(74) *Attorney, Agent, or Firm* — The Webb Law Firm

(57) ABSTRACT

The present disclosure provides an oral drug composition including a prodrug and a carrier. The prodrug bonds an active drug to a spacer with a covalent bond, in which the spacer has a disulfide bond. The carrier is for carrying the prodrug with an efficient amount, and the carrier includes a β-1,3-D-glucan.

8 Claims, 5 Drawing Sheets
(3 of 5 Drawing Sheet(s) Filed in Color)

ORAL DRUG COMPOSITION AND USE THEREOF

CROSS-REFERENCE TO RELATED APPLICATION

This application claims priority to Taiwanese Patent Application No. 108132636 filed Sep. 10, 2019, the disclosure of which is hereby incorporated by reference in its entirety.

BACKGROUND OF THE INVENTION

Field of the Invention

The present disclosure relates to a composition and a use thereof. More particularly, the present disclosure relates to a pharmaceutical composition characterized by special physical form thereof and a use thereof.

Description of Related Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for twenty-seven consecutive years.

Conventional cancer treatments include surgery, radiation therapy, and drug treatment (including chemotherapy drug, target treatment drug and hormone treatment drug). However, surgery cannot completely remove tumor cells in most cases, which may cause tumor recurrence in patients; radiation therapy often causes extremely serious side effects on normal tissues. Drug treatment is one of three treatment methods that can achieve systemic treatment effects.

The general drug administration methods include injection administrations (such as intravenous injection, intramuscular injection or subcutaneous injection, etc.), oral administrations (such as oral administration through the gastrointestinal tract, sublingual tablets and oral tablets, etc.) and external administrations (such as transdermal mucosal medication, transdermal absorption medication, transnasal mucosa or pulmonary respiratory tract medication, etc.). Oral administration is to swallow the drug through the gastrointestinal mucosa and transport it to various parts of the body through the bloodstream to make it function in the body. Oral administration eliminates the need for needles and is convenient to use, which is conducive to patient self-management, so it is considered a promising way of administration.

However, there are still problems with oral administration. For example, drug absorption is slow and irregular, and oral administration is also prone to encounter the mucosal barrier formed by tightly arranged epithelial cells in the intestine and reduce its effectiveness. Therefore, how to develop a new type of oral drug composition that can effectively deliver the loaded active drug to the body's target has become important development goals in the field of pharmacy today.

SUMMARY OF THE INVENTION

According to one aspect of the present disclosure, an oral drug composition is provided. The oral drug composition includes a prodrug and a carrier. The prodrug bonds an active drug to a spacer with a covalent bond, in which the spacer has a disulfide bond. The carrier is for carrying the prodrug with an efficient amount, and the carrier includes a $\beta$-1,3-D-glucan.

According to another aspect of the present disclosure, a method for treating a cancer is provided. The method includes administering an effective amount of the aforementioned oral drug composition to a subject in need for a treatment of the cancer.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DESCRIPTION OF THE INVENTION

Figure 1A:
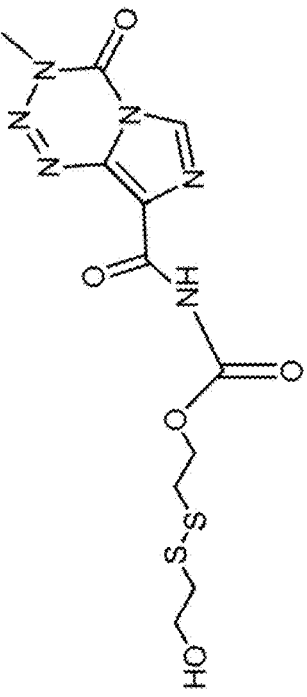
FIGS. 1A and 1B are flow charts showing a fabrication process of an oral drug composition according to Example 1 of the present disclosure.
Figure 1A:
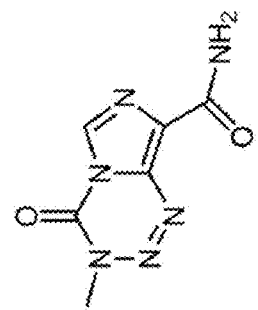

The following descriptions of particular embodiments and examples are provided by way of illustration and not by way of limitation. Those skilled in the art will readily recognize a variety of noncritical parameters that could be changed or modified to yield essentially similar results.

Unless otherwise stated, the meanings of the scientific and technical terms used in the specification are the same as those of ordinary skill in the art. Furthermore, the nouns used in this specification are intended to cover the singular and plural terms of the term unless otherwise specified.

The term "individual" or "patient" refers to an animal that is capable of administering an oral drug delivery system of the present disclosure. Preferably, the animal is a mammal.

The term "about" means that the actual value falls within the acceptable standard error of the average, as determined by person having ordinary skill in the art. The scope, number, numerical values, and percentages used herein are modified by the term "about" unless example or otherwise stated. Therefore, unless otherwise indicated, the numerical values or parameters disclosed in the specification and the claims are approximate values and can be adjusted according to requirements.

Oral Drug Composition

An oral drug composition is provided in the present disclosure. The oral drug composition includes a prodrug and a carrier. The prodrug bonds an active drug to a spacer with a covalent bond, in which the spacer has a disulfide bond. The active drug can include temozolomide, carboplatin, doxorubicin, tamoxifen, irinotecan, paclitaxel, cilengitide, vorinostant or sorafenib. The spacer can be represented by Formula (I), Formula (II) or Formula (III):

of Example 1 of the present disclosure. The detailed fabrication process is as follows. First, triphosgene and N, N-Diisopropylethylamine (DIPEA) are used to graft dithioethanol onto temozolomide to form the precursor temozolomide (prodrug), and then the β-1,3-D-glucan is carboxylated with sodium 2-chloroacetate. The precursor

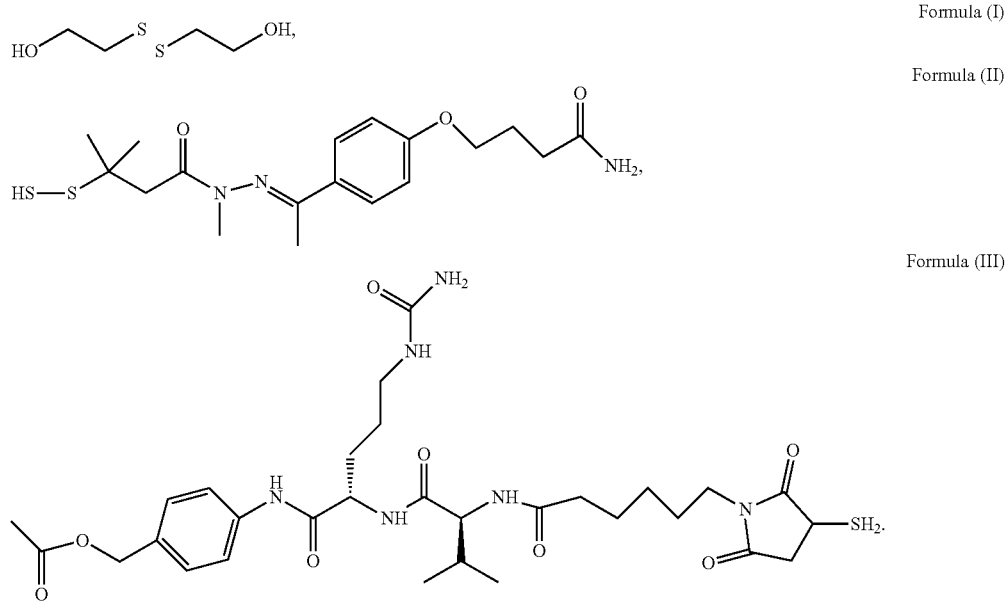

Formula (I)

Formula (II)

Formula (III)

The carrier is for carrying the prodrug with an efficient amount, and the carrier includes a β-1,3-D-glucan. The carrier can be a yeast capsule or the β-1,3-D-glucan extracted from a yeast. The yeast capsule is composed of a β-glucan cell-wall shell that removes a cytoplasm from the yeast. For example, the yeast can be destroyed by acid and alkali, and then its cytoplasm can be removed by isopropyl alcohol and acetone solution. Preferably, the yeast can be *Saccharomyces cerevisiae, Candida albicans, Rhodotorula rubra* or *Torulopsis utilis*.

Examples

I. Fabrication of Oral Drug Composition of the Present Disclosure

An oral drug composition of Example 1 is fabricated in this experiment first. The active drug used in the oral drug composition of Example 1 is temozolomide, the spacer is represented by Formula (I):

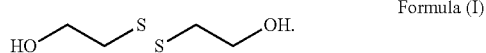

Formula (I)

The carrier is the β-1,3-D-glucan extracted from the *Saccharomyces cerevisiae*. Furthermore, the *Saccharomyces cerevisiae* is destroyed by acid and alkali, and its cytoplasm can be removed by isopropyl alcohol and acetone solution to obtain the β-glucan cell-wall shell. Then the β-1,3-D-glucan is obtained by degradation of the β-glucan cell-wall shell.

Figure 1B:
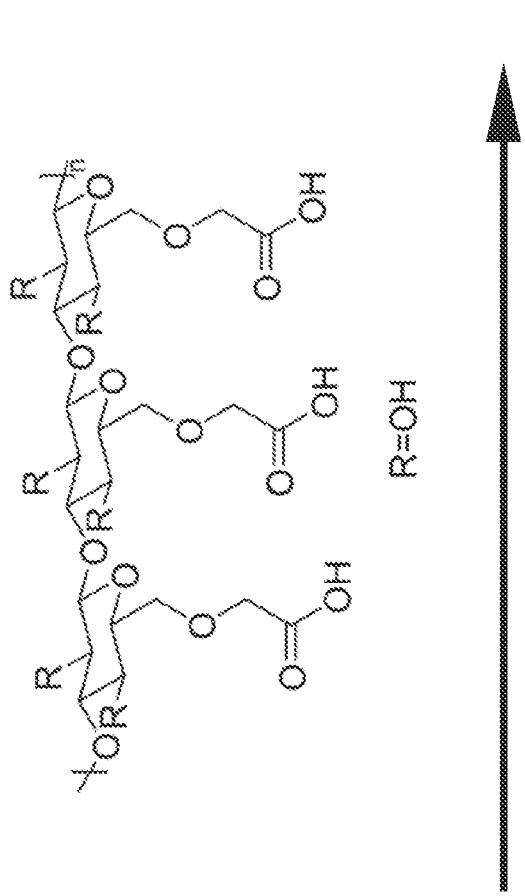
Figure 1B:
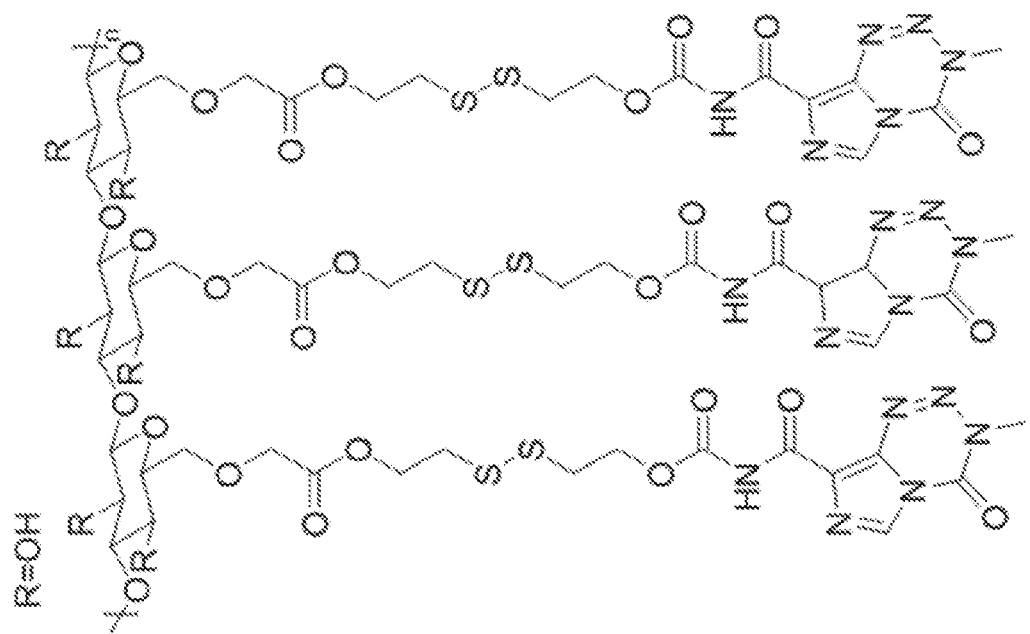

Please refer to FIGS. 1A and 1B, which are flow charts showing a fabrication process of the oral drug composition temozolomide is grafted to the carboxylated β-1,3-D-glucan by dehydration through esterification to obtain the oral drug composition of Example 1 coated with the precursor temozolomide (hereinafter referred to as Example 1).

II. In Vivo Transport Route of Oral Drug Composition

The ability of the oral drug composition of the present disclosure to improve the transportation of the oral drug through the mucosal barrier is examined in this experiment. Further, whether the oral drug composition of the present disclosure can enter the blood circulation through the lymphatic system to the thymus, pass the blood-brain barrier and enter the brain, and transport the prodrug encapsulated therein into the brain is also studied in this experiment. First, Example 1 is labeled with FITC (hereafter referred to as FITC-Example 1). The test animals in the treated group are orally treated with FITC-Example 1, and the test animals are sacrificed 6 hours after oral administration. The distribution of FITC-Example 1 in the brains, hearts, lungs, livers, spleens, pancreas and kidneys of the test animals are confirmed using an in vivo imaging system (IVIS). The untreated test animals are as a control group. The test animals used in this experiment are 6 to 8 weeks old C57BL/6 mice (BioLASCO Taiwan).

Figure 2:
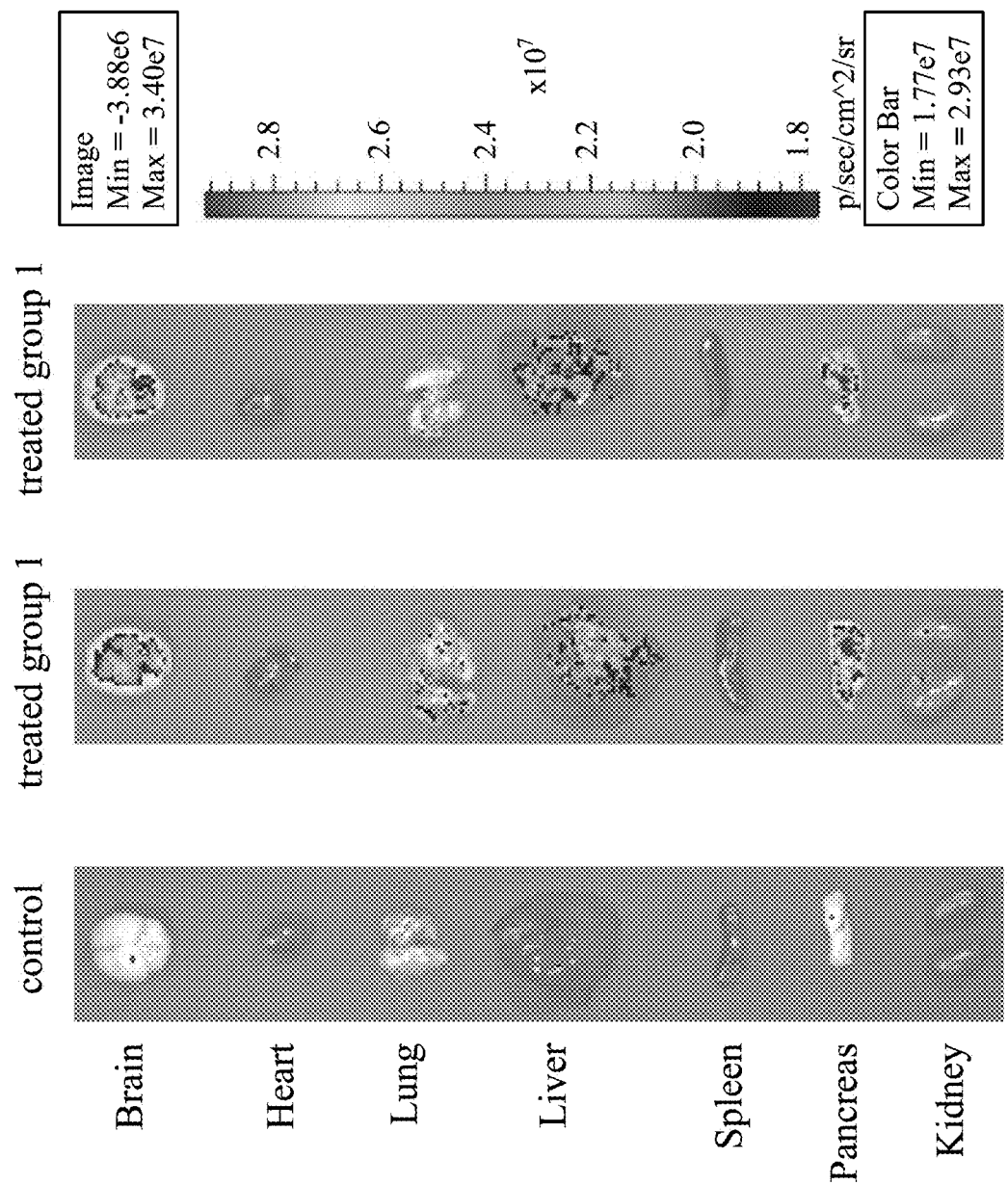
FIG. 2 shows analytical results of in vivo imaging system of brain, heart, lung, liver, spleen, pancreas and kidney after administration with the oral drug composition of Example 1 of the present disclosure.

Please refer to FIG. 2, which shows analytical results of in vivo imaging system of brain, heart, lung, liver, spleen, pancreas and kidney after administration with the oral drug composition of Example 1 of the present disclosure. In FIG. 2, the distributions of the FITC-Example 1 in the brain, lung, liver and pancreas are detected in the treated group orally treated with FITC-Example 1, while the FITC signal does not be detected in the control group. The results indicate that the oral drug composition of the present disclosure has the ability to pass the mucosal barrier and deliver the prodrug encapsulated therein to the body tissues, and even the brain.

III. Therapeutic Effect of Oral Drug Composition on Treating Cancer

A mouse model of malignant glioma in situ is used to test the therapeutic effect of the oral drug composition of the present disclosure on treating cancer. The mouse model of malignant glioma in situ is established by injecting $4 \times 10^4$ ALTS1C1 cells into the brain of 6 to 8-week-old C57BL/6 mice. After 14 days, it is confirmed that the tumor diameter reached about 5 mm (or tumor volume reached 50-450 mm$^3$) to complete the establishment of the mouse model of malignant glioma in situ. The malignant glioma in situ mice in the treated group are orally treated with FITC-Example 1, and the malignant glioma in situ mice are sacrificed 6 hours after oral administration. The distribution of FITC-Example 1 in the brain, tumor, heart, lung, liver, spleen, pancreas and kidney of the malignant glioma in situ mice are confirmed using an in vivo imaging system (IVIS), and the tissues are taken to take photographs to test whether the oral drug composition of the present disclosure has the therapeutic effect on treating cancer. The malignant glioma in situ mice orally treated with saline are as a control group.

Figure 3B:
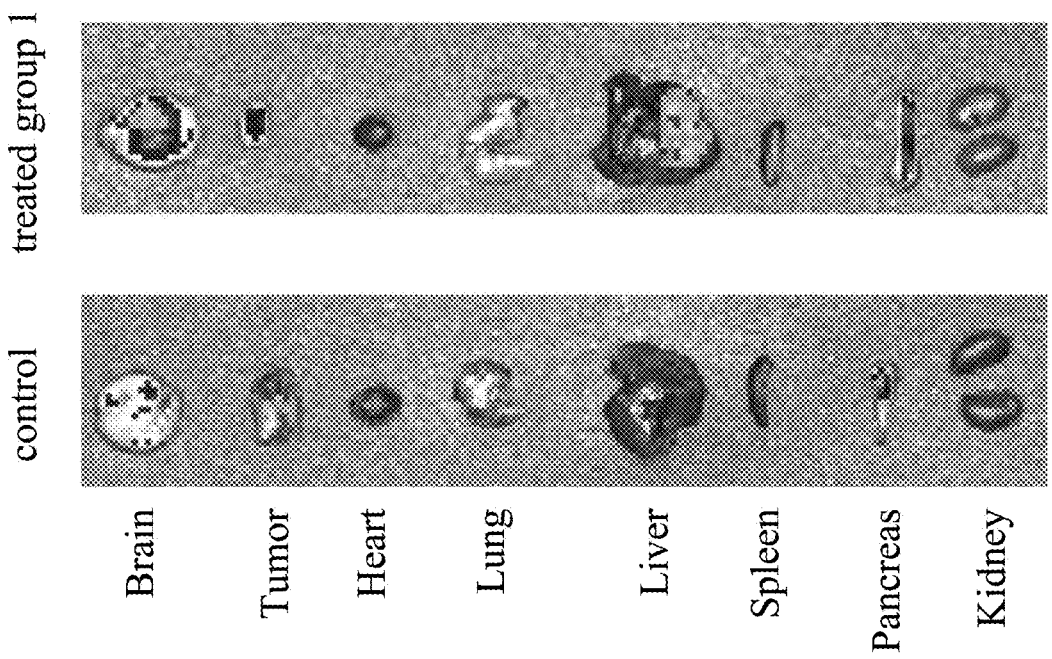
FIG. 3B shows analytical results of in vivo imaging system of brain, tumor, heart, lung, liver, spleen, pancreas and kidney after treatment with the oral drug composition of Example 1 of the present disclosure.
Figure 3A:
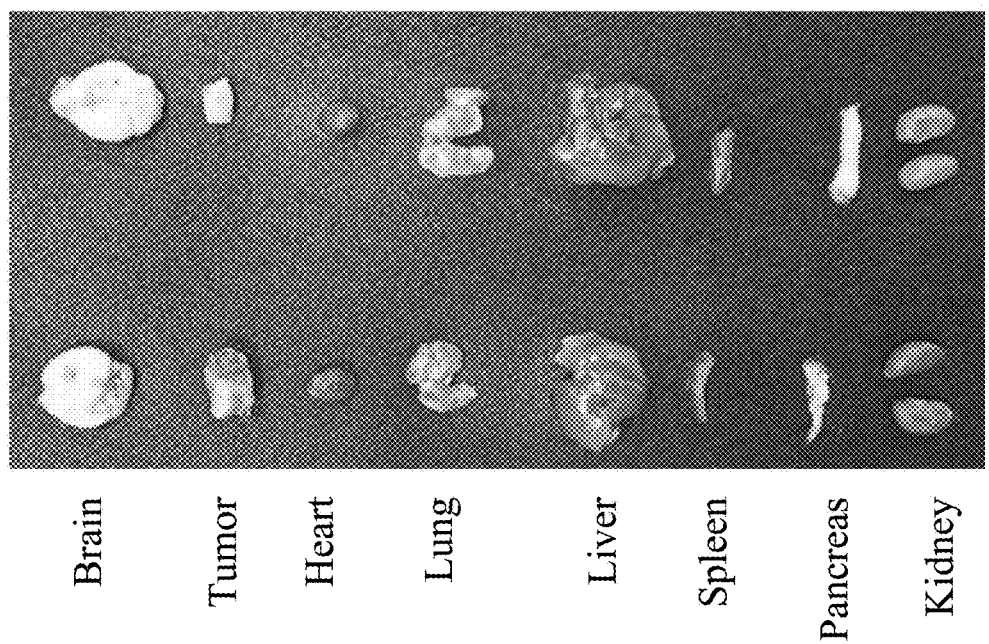
FIG. 3A shows photograph of brain, tumor, heart, lung, liver, spleen, pancreas and kidney after treatment with the oral drug composition of Example 1 of the present disclosure.

Please refer to FIGS. 3A and 3B. FIG. 3A shows photograph of brain, tumor, heart, lung, liver, spleen, pancreas and kidney after treatment with the oral drug composition of Example 1 of the present disclosure. FIG. 3B shows analytical results of in vivo imaging system of brain, tumor, heart, lung, liver, spleen, pancreas and kidney after treatment with the oral drug composition of Example 1 of the present disclosure. In FIGS. 3A and 3B, the distributions of the FITC-Example 1 in the brain, tumor, lung, liver and pancreas are detected in the treated group orally treated with FITC-Example 1, while the FITC signal does not be detected in the control group. In addition, compared with the control group, the tumor size of the malignant glioma in situ mice in the treated group is significantly reduced. The results indicate that the oral drug composition of the present disclosure has the ability to pass the mucosal barrier and deliver the temozolomide encapsulated therein to the brain to achieve an effective therapeutic effect.

Figure 4A:
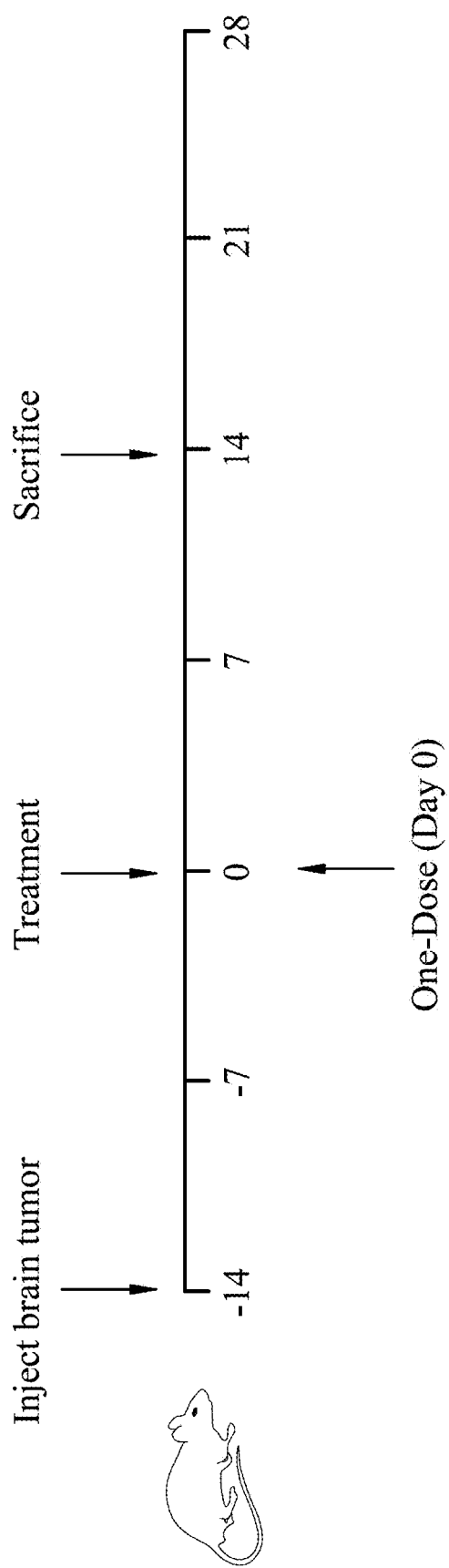
FIG. 4A is a schematic diagram of an animal therapeutic test of the oral drug composition of the present disclosure.

Please refer to FIG. 4A, which is a schematic diagram of an animal therapeutic test of the oral drug composition of the present disclosure. In the animal therapeutic test, the C57BL/6 mice are inoculated with $4 \times 10^4$ ALTS1C1 cells into the brain to generate brain tumors 14 days before oral administration, and it is confirmed that the tumor diameter reached approximately 5 mm (or tumor volume reached 50-450 mm$^3$) to complete the establishment of the mouse model of malignant glioma in situ. On Day 0, the malignant glioma in situ mice in the treated group are treated with one dose by orally administering Example 1. On Day 14, the malignant glioma in situ mice are sacrificed, and the tumor tissues are removed for photographing. The malignant glioma in situ mice orally treated with saline are as a control group.

Figure 4B:
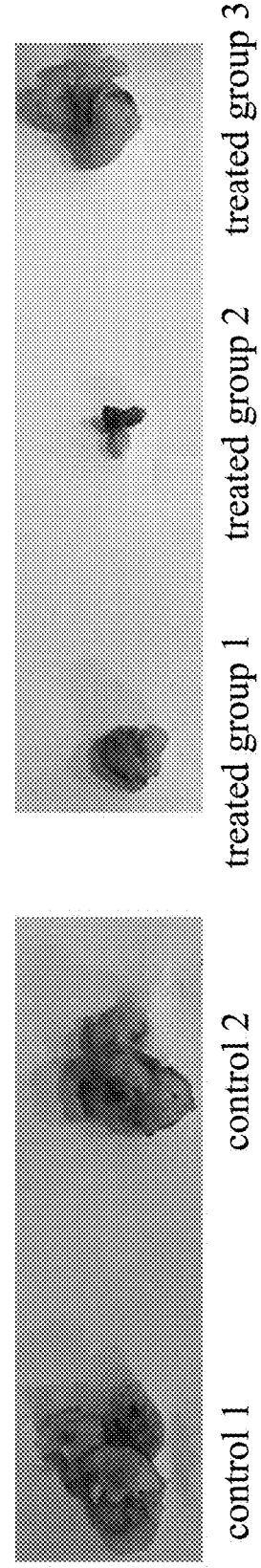
FIG. 4B shows photographs of tumors before and after treatment with the oral drug composition of Example 1 of the present disclosure.

Please refer to FIG. 4B, which shows photographs of tumors before and after treatment with the oral drug composition of Example 1 of the present disclosure. Compared the malignant glioma in situ mice in the treated group orally administered with Example 1 with the malignant glioma in situ mice in the control group, the tumor size of the malignant glioma in situ mice in the treated group is significantly reduced, especially the malignant glioma in situ mice in the treated group 2. The results also indicate that the oral drug composition of the present disclosure has the ability to pass the mucosal barrier and deliver the temozolomide encapsulated therein to the brain to achieve an effective therapeutic effect.

In summary, the oral drug composition of the present disclosure can use a spacer having a disulfide bond to make the prodrug less active than the active drug. After entering the body, the disulfide bond of the prodrug can be broken by glutathione (GSH) to form the active drug. Therefore, the active drug is released at a reasonable action site so that the active drug has a sufficient concentration at the target site. The carrier including the β-1,3-D-glucan can target M cells in the intestinal tract, increasing transepithelial absorption of the oral drug composition, followed by subsequent endocytosis in local macrophages, ultimately accumulating in the mesenteric lymph nodes. Further, after being endocytosed by macrophages, the oral drug composition of the present disclosure can enter the blood circulation through the lymphatic system to the thymus, then pass the blood-brain barrier and enter the brain, and deliver the prodrugs encapsulated therein to the brain. Therefore, the oral drug composition of the present disclosure can deliver brain drugs by oral administration. Further, the oral drug composition can be used as an anticancer drug. For example, the oral drug composition can be used as a drug to inhibit proliferation of cancer cell.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:
1. An oral drug composition, comprising:
   a prodrug bonding an active drug to a spacer with a covalent bond; and
   a carrier for carrying the prodrug with an efficient amount, wherein the carrier comprises a carboxylated β-1,3-D-glucan covalently linked to the spacer;
   wherein the active drug has an amine group and the spacer is represented by Formula (I):

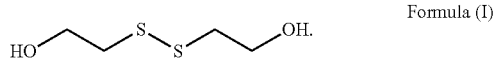

Formula (I)

2. The oral drug composition of claim 1, wherein the active drug is a hydrophobic drug.
3. The oral drug composition of claim 2, wherein the hydrophobic drug comprises temozolomide, carboplatin, doxorubicin, tamoxifen, paclitaxel, cilengitide, vorinostant or sorafenib.
4. The oral drug composition of claim 1, wherein carboxylated β-1,3-D-glucan is obtained by carboxylation of a β-1,3-D-glucan with sodium 2-chloroacetate.
5. The oral drug composition of claim 4, wherein the β-1,3-D-glucan is extracted from a yeast.

6. The oral drug composition of claim 5, wherein the yeast is *Saccharomyces cerevisiae, Candida albicans, Rhodotorula rubra* or *Torulopsis utilis*.

7. A method for treating a cancer comprising administering an effective amount of the oral drug composition of claim 1 to a subject in need for a treatment of the cancer.

8. The method of claim 7, wherein the cancer is a malignant glioma.

* * * * *

UNITED STATES PATENT AND TRADEMARK OFFICE
CERTIFICATE OF CORRECTION

PATENT NO. : 11,278,630 B2
APPLICATION NO. : 16/810983
DATED : March 22, 2022
INVENTOR(S) : Hsing-Wen Sung et al.

It is certified that error appears in the above-identified patent and that said Letters Patent is hereby corrected as shown below:

In the Claims

Column 6, Lines 53-56, Claim 1, delete "HO~S-S~OH" and insert -- HO~S~S~OH --

Column 6, Line 61, Claim 3, delete "vorinostant" and insert -- vorinostat --

Signed and Sealed this
Twenty-fourth Day of May, 2022

*Katherine Kelly Vidal*

Katherine Kelly Vidal
*Director of the United States Patent and Trademark Office*